United States Patent
Zilberman et al.

(10) Patent No.: US 6,611,718 B2
(45) Date of Patent: Aug. 26, 2003

(54) HYBRID MIDDLE EAR/COCHLEA IMPLANT SYSTEM

(75) Inventors: Yitzhak Zilberman, 23462 Thornewood Dr., Santa Clarita, CA (US) 91321; Joseph H. Schulman, Santa Clarita, CA (US)

(73) Assignees: Yitzhak Zilberman, Santa Clarita, CA (US); Joseph Schulman, Santa Clarita, CA (US)

( * ) Notice: Subject to any disclaimer, the term of this patent is extended or adjusted under 35 U.S.C. 154(b) by 0 days.

(21) Appl. No.: 09/881,832

(22) Filed: Jun. 15, 2001

(65) Prior Publication Data

US 2001/0056291 A1 Dec. 27, 2001

Related U.S. Application Data

(60) Provisional application No. 60/212,517, filed on Jun. 19, 2000.

(51) Int. Cl.$^7$ .................................................. A61N 1/00
(52) U.S. Cl. ........................................... 607/57; 600/25
(58) Field of Search .............................. 600/25; 607/55, 607/56, 57

(56) References Cited

U.S. PATENT DOCUMENTS

| 5,906,635 | A | * | 5/1999 | Maniglia |
| 5,913,815 | A | | 6/1999 | Ball et al. |
| 6,216,040 | B1 | | 4/2001 | Harrison |
| 6,259,951 | B1 | * | 7/2001 | Kuzma et al. |
| 6,272,382 | B1 | | 8/2001 | Faltys et al. |
| 6,308,101 | B1 | | 10/2001 | Faltys et al. |

* cited by examiner

Primary Examiner—Scott M. Getzow
(74) Attorney, Agent, or Firm—Lee J. Mandell; K. Cyrus Khosravi

(57) ABSTRACT

A system for enhancing hearing comprised of both a middle ear implant and a cochlear implant. The system directs signals relating to lower frequency sound to the middle ear implant and signals relating to higher frequency sound to the cochlear implant. The middle ear implant comprises an electrically driven actuator, e.g., a speaker, for vibrating the middle ear ossicles via air conducted sound energy or a mechanical transducer for physically contacting and mechanically vibrating the ossicles. The cochlear implant includes electrodes preferably implanted at a shallow level at the basal end of the cochlea.

13 Claims, 1 Drawing Sheet

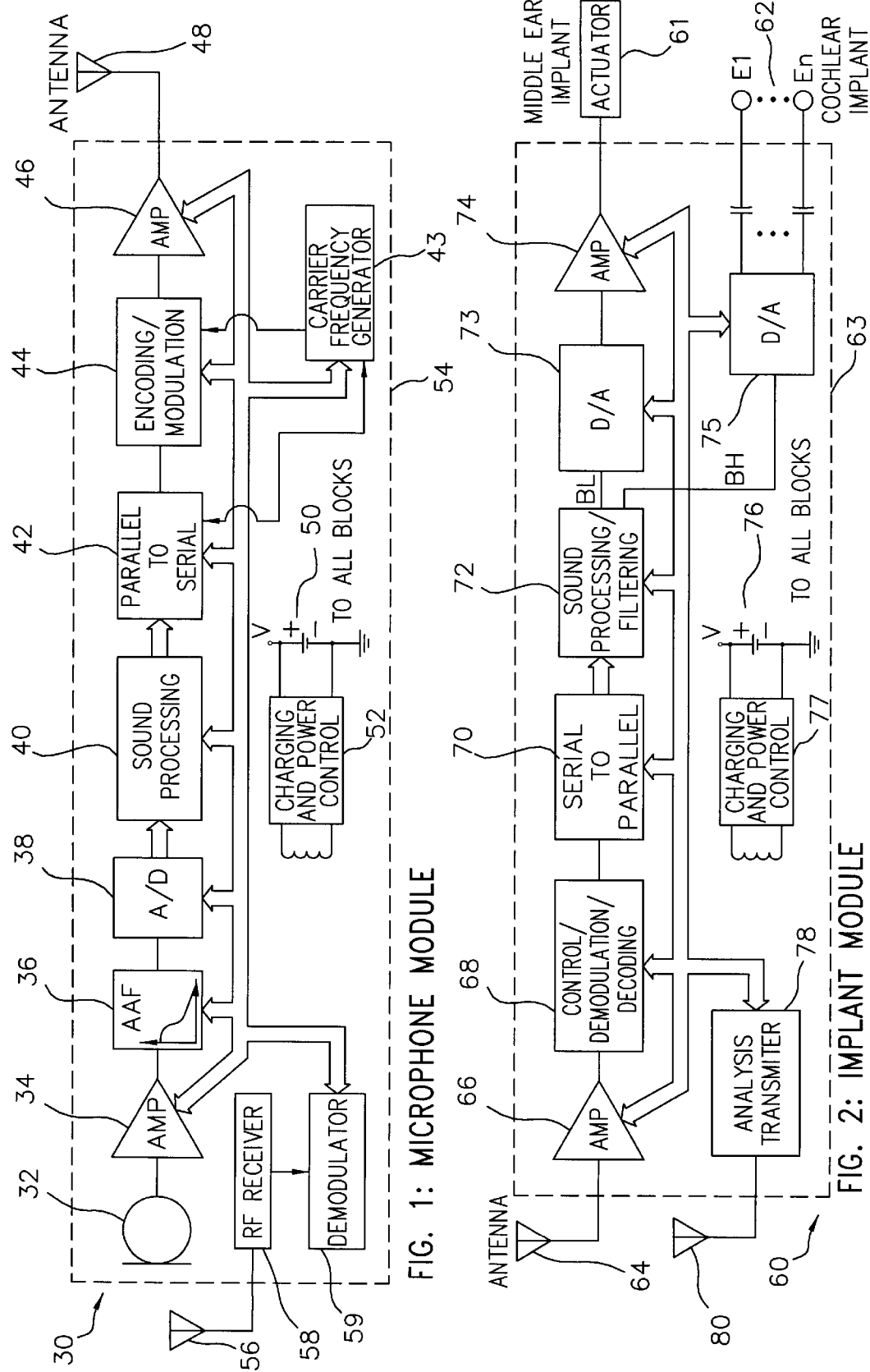

HYBRID MIDDLE EAR/COCHLEA IMPLANT SYSTEM

RELATED APPLICATIONS

This application claims the benefit of U.S. Provisional Application No. 60/212,517 filed Jun. 19, 2000.

FIELD OF THE INVENTION

This invention relates generally to a system and method for enhancing hearing in patients suffering from sensorineural hearing deficiencies and more particularly to a system including a middle ear implant for handling lower frequency sounds and a cochlear implant for handling higher frequency sounds.

BACKGROUND OF THE INVENTION

Hearing loss is frequently categorized as being either "conductive hearing loss" or "sensorineural hearing loss". Conductive hearing loss typically refers to middle ear impairment and generally results from damage to the tympanic membrane and/or middle ear ossicles. Sensorineural hearing loss is frequently attributable to a reduction in function of hair cells within the cochlea. When sufficiently severe, sensorineural hearing loss can be mitigated by implanting electrodes in the cochlea to electrically stimulate the auditory nerve. When less severe, hearing loss can be mitigated by enhanced activation of the middle ear mechanism. For example, the prior art describes various electrically driven actuator devices for physically contacting and mechanically vibrating the middle ear ossicles.

Great strides have been made in the development of cochlear implant systems for restoring hearing in people suffering from severe sensorineural hearing loss. Such systems are typically comprised of an implant housing containing implant electronics for driving an array of electrodes which are surgically inserted into the cochlea. The implant electronics is typically driven by sound processing electronic circuitry which is generally, but not necessarily, contained in a housing worn externally by the patient. A microphone carried by the patient supplies electric signals to the input of the sound processing circuitry. Typical sound processing circuitry and implant electronics provide for multiple frequency channels.

In order to provide for good speech comprehension, reception of sound across a broad frequency range from about 100 to about 16000 Hz is desirable. Mechanical stimulators such as conventional hearing aids and middle ear implants carry sound with high fidelity up to around 4000 Hz. The basal end of the cochlea is primarily sensitive to higher frequency stimulation and is well suited for handling sound above 4000 Hz.

SUMMARY OF THE INVENTION

The present invention is directed to a system for enhancing hearing comprised of both a middle ear implant and a cochlear implant. The system directs signals relating to lower frequency sound to the middle ear implant and signals relating to higher frequency sound to the cochlear implant.

In accordance with the preferred embodiment, the middle ear implant comprises an electrically driven actuator, e.g., a speaker for vibrating the middle ear ossicles via air conducted sound energy or a mechanical transducer for physically contacting and mechanically vibrating the ossicles.

A preferred cochlear implant includes electrodes implanted at a shallow level at the basal end of the cochlea.

BRIEF DESCRIPTION OF THE DRAWINGS

FIG. 1 is a block diagram of an exemplary microphone module in accordance with the invention; and FIG. 2 is a block diagram in accordance with the invention depicting a system including both middle ear and cochlea implants.

DETAILED DESCRIPTION OF THE PREFERRED EMBODIMENTS

Attention is now directed to FIG. 1 which illustrates an exemplary microphone module 30 intended to be either implanted in a patient's body or worn externally. The module 30 is comprised of a microphone 32, an amplifier 34, a filter 36, e.g., antialiasing, an analog to digital converter 38, a digital sound processing circuit 40, a parallel to serial converter 42, and an encoding/modulation transmitter circuit 44. The carrier frequency generator 43 is combined with the signal from the parallel to serial converter 42 to produce an encoded and modulated carrier radio frequency signal that is transmitted by the antenna 48. The output of the transmitter circuit 44 is coupled through amplifier 46 to the antenna 48. The blocks of the microphone module 30 depicted in FIG. 1 are all powered by a battery 50. The battery is preferably of the rechargeable type, e.g., a lithium ion battery, which can be charged by charging and power control circuit 52 from, for example, energy extracted from an alternating magnetic field provided by an external source (not shown). All of the elements of FIG. 1 are preferably contained in a housing 54 which is hermetically sealed and suitable for implanting in a patient's body near to the middle ear and inner ear. Alternatively, the housing 54 can be worn externally, as on a patient's belt or behind the patient's ear.

The microphone module 30 preferably also contains an RF receiver 58 which detects a signal from the receive antenna 56. An external fitting transmitter (not shown) can be used by a clinician to program the microphone module 30 for optimum performance, for the particular patient. This signal received from the RF receiver 58 (via antenna 56) is demodulated by the demodulator 59 which is used to set various parameters in one or more of the electronics circuits in module 30. This may include the gain in amplifier 34, the frequency roll off points in filter 36, the speed of the A/D converter 38, the compression and filtering of the sound processing circuit 40, the phase of synchronization of the parallel to serial converter 42, the frequency of carrier frequency generator 43, the degree and type of encoding and modulation of encoding/modulation circuit 44, the gain of power amplifier 46, and the charging and discharging parameters of the charging and power control circuit 52. Note that the antennas 56 and 48 can in fact comprise a single physical antenna with a transmit receive switch (not shown).

In use, sound energy detected by microphone 32 is, after filtering, preferably converted to digital form and appropriately processed by sound processing circuit 40 to best mitigate the particular hearing impairment of the patient. The resulting digital signal produced by sound processing circuit 40 is then preferably converted to an analog signal and used to modulate an RF carrier signal in circuit 44. Alternatively, the carrier can be modulated in digital form and then converted to analog which is then applied to the power amplifier 46 and sent to antenna 48. The foregoing can be accomplished in various alternative ways readily known to those skilled in the art.

Attention is now directed to FIG. 2 which illustrates an implant module 60 in accordance with the invention for driving an actuator 61 implanted in a patient's middle ear and an array comprised of a plurality of electrodes 62 implanted in a patient's cochlea. The actuator 61 is electrically driven to vibrate the middle ear ossicles and can comprise a mechanical device which physically contacts the ossicles or a speaker which impacts the ossicles with air conducted sound energy. The middle ear implant 61 is intended to handle the lower portion (e.g., to about 4000 Hz) of the speech frequency range (about 100 Hz to 16000 Hz) and the cochlear implant 62 is intended to handle the upper portion of the range (e.g., to about 16000 Hz). When appropriate, the range can be extended, e.g., to about 20000 Hz, to match the normal hearing of a child. The electrodes 62 can be inserted to a shallow level at the basal end of the cochlea for stimulating the higher frequency sounds.

The implant module 60 includes a hermetically sealed housing 63 carrying a receive antenna 64 for communicating with the aforementioned antenna 48 of the microphone module 30 and a transmit antenna 80 to communicate analysis parameters to the clinician. The antenna 64 is connected via RF amplifier 66 to the control/demodulation/decoding circuit 68. The output of circuit 68 is converted from serial to parallel form in block 70 and then processed in sound processing/filtering block 72. Block 72 performs sound processing in accordance with known techniques and then functionally separates information signals relating to a lower frequency band BL and information signals relating to a higher frequency band BH. The BL signals drive digital to analog converter 73 which via amplifier 74 drives aforementioned middle ear implant actuator 61. The BH signals drive digital to analog converter 75 which provides signals to stimulate electrodes 62 implanted in the cochlea. All of the blocks in FIG. 2 are intended to be driven by a battery 76 and charging circuit 77, similar to aforementioned battery 50 and charging circuit 52. Also control/demodulator/decoding circuit 68 also determines which electronic module is accessed by analysis transmitter 78 to send audio data and parameter signals to the clinician fitting system receiver (not shown) to guide the clinician in programming the circuitry within, e.g., the control/demodulation/decoding circuit 68.

From the foregoing, it should now be apparent that applicants have disclosed a system and method for improving the hearing of patients suffering from sensorineural hearing deficiencies utilizing a hybrid system comprised of both middle ear and cochlear implants for respectively handling different frequency bands. Although a preferred embodiment of the invention has been disclosed herein it should be recognized that variations and modifications will readily occur to those skilled in the art. For example only, although the preferred disclosed embodiment contemplates that communication between the microphone module 30 and implant module 60 be via a wireless channel, typically radio frequency, it may be more appropriate in some cases to connect the module 30 to the module 60 by wire. It is also pointed out that although FIG. 2 suggests that the signals for the low and high frequency bands be separated in the digital domain, alternatively band pass filtering could be performed in the analog domain.

What is claimed is:

1. A system for enhancing a patient's hearing capability, said system comprising:
   an electrically actuatable actuator adapted to be mounted in said patient's middle ear actuatable to vibrate said patient's ossicles;
   at least one electrode adapted to be implanted adjacent to said patient's cochlea energizable to stimulate said cochlea; and
   a sound processor for supplying output signals of a lower frequency to said electrically actuatable actuator and of a higher frequency to said electrode.

2. The system of claim 1, wherein said electrically actuatable actuator comprises a transducer for producing sound energy for vibrating said patient's ossicles.

3. The system of claim 1, wherein said electrically actuatable actuator comprises a transducer for physically vibrating said patient's ossicles.

4. The system of claim 1, wherein said sound processor supplies signals within low frequency band BL to said electrically actuatable actuator and signals within a high frequency band BH to said electrode; and
   wherein said low frequency band BL has an upper frequency cutoff of about 4000 Hz and said high frequency band BH has a lower frequency cutoff of about 4000 Hz.

5. The system of claim 1, further including:
   a microphone module responsive to sound energy incident thereon for producing an output signal representative of said sound energy;
   means for coupling said microphone module output signal to the input of said sound processor.

6. The system of claim 5, wherein said coupling means comprises a radio frequency communication link coupling said microphone module output to said sound processor input.

7. In combination:
   an electrically actuatable transducer adapted to be mounted in a patient's middle ear;
   a source of first electrical signals representing sound energy within a low frequency band BL;
   means for applying said first electrical signals to said electrically actuatable transducer for vibrating said patient's ossicles;
   an electrically energizable electrode array adapted to be implanted adjacent to a patient's cochlea;
   a source of second electrical signals representing sound energy within a high frequency band BH; and
   means for applying said second electrical signals to said electrically energizable electrode array for stimulating said patient's cochlea.

8. The combination of claim 7, wherein said electrically actuatable transducer is configured to respond to said first electrical signals for producing sound energy for vibrating said patient's ossicles.

9. The combination of claim 7, wherein said electrically actuatable transducer is configured to respond to said first electrical signals for physically vibrating said patient's ossicles.

10. The combination of claim 7, wherein said low frequency band BL has an upper cutoff frequency of about 4000 Hz and said high frequency band BH has a lower cutoff frequency of about 4000 Hz.

11. A method of enhancing a patient's hearing comprising:
   mounting an electrically actuatable transducer in a patient's ear;
   supplying first electrical signals representative of sound energy within a low frequency band BL to said electrically actuatable transducer for vibrating said patient's ossicles;
   mounting an electrode array adjacent to said patient's cochlea; and
   supplying second electrical signals representative of sound energy within a high frequency band BH to said electrode array for stimulating said patient's cochlea.

12. The method of claim 11, further including:
producing source electrical signals representative of incident sound energy across a spectrum comprised of frequency bands BL and BH; and
processing said source electrical signals into said first electrical signals and said second electrical signals.

13. The method of claim 11, wherein said low frequency band BL has an upper cutoff frequency of about 4000 Hz and said high frequency band BH has a lower cutoff frequency of about 4000 Hz.

* * * * *